(12) United States Patent
Bukkapatnam et al.

(10) Patent No.: US 11,980,720 B2
(45) Date of Patent: May 14, 2024

(54) WEARABLE THERAPEUTIC INTERVENTION DEVICE FOR SLEEP DISORDERS AND METHODS OF USE THEREOF

(71) Applicant: The Texas A&M University System, College Station, TX (US)

(72) Inventors: Satish Bukkapatnam, College Station, TX (US); Kahkashan Afrin, College Station, TX (US); Vu Nguyen, College Station, TX (US)

(73) Assignee: THE TEXAS A&M UNIVERSITY SYSTEM, College Station, TX (US)

( * ) Notice: Subject to any disclaimer, the term of this patent is extended or adjusted under 35 U.S.C. 154(b) by 456 days.

(21) Appl. No.: 16/762,096

(22) PCT Filed: Dec. 7, 2018

(86) PCT No.: PCT/US2018/064408
§ 371 (c)(1),
(2) Date: May 6, 2020

(87) PCT Pub. No.: WO2019/113411
PCT Pub. Date: Jun. 13, 2019

(65) Prior Publication Data
US 2020/0353203 A1  Nov. 12, 2020

Related U.S. Application Data

(60) Provisional application No. 62/596,663, filed on Dec. 8, 2017.

(51) Int. Cl.
*A61M 21/02* (2006.01)
*A61B 5/00* (2006.01)
(Continued)

(52) U.S. Cl.
CPC ........... *A61M 21/02* (2013.01); *A61B 5/0205* (2013.01); *A61B 5/7221* (2013.01);
(Continued)

(58) Field of Classification Search
CPC . A61M 21/00–02; A61B 5/4806–4818; A61B 5/02416
See application file for complete search history.

(56) References Cited

U.S. PATENT DOCUMENTS

2008/0103407 A1* 5/2008 Bolea ................... A61N 1/3606
607/42
2014/0180036 A1 6/2014 Bukkapatnam et al.
(Continued)

FOREIGN PATENT DOCUMENTS

CN           205338424 U  *  6/2016
DE           10024103 A1  * 11/2001  ........... A61B 5/0205
(Continued)

OTHER PUBLICATIONS

PCT/US2018/064408 International Search Report and Written Opinion dated Feb. 7, 2019 (15 p.).
(Continued)

*Primary Examiner* — Thaddeus B Cox
(74) *Attorney, Agent, or Firm* — CONLEY ROSE, P.C.

(57) ABSTRACT

A therapeutic device comprises a sensor positioned proximate to a user and configured to receive a plurality of signals, and a processor coupled to the sensor and configured to determine a biomarker describing a biological characteristic of the user based on the plurality of signals, and determine whether the user is likely to experience an impending sleep disorder episode within a predetermined period of time based on the biomarker.

21 Claims, 11 Drawing Sheets

(51) Int. Cl.
*A61B 5/0205* (2006.01)
*A61B 5/024* (2006.01)
*A61B 5/1455* (2006.01)
*A61B 5/08* (2006.01)
*A61M 21/00* (2006.01)

(52) U.S. Cl.
CPC ......... *A61B 5/02433* (2013.01); *A61B 5/0816* (2013.01); *A61B 5/14552* (2013.01); *A61B 5/4818* (2013.01); *A61M 2021/0022* (2013.01); *A61M 2205/3303* (2013.01)

(56) References Cited

U.S. PATENT DOCUMENTS

| | | | |
|---|---|---|---|
| 2016/0113838 A1* | 4/2016 | Paydarfar | A61B 5/7275 601/46 |
| 2016/0151603 A1* | 6/2016 | Shouldice | G10L 15/26 600/26 |
| 2017/0143249 A1 | 5/2017 | Davis et al. | |
| 2017/0156593 A1* | 6/2017 | Ferber | A61B 5/0806 |
| 2017/0165101 A1* | 6/2017 | Davidian | A61B 5/4818 |
| 2017/0311825 A1 | 11/2017 | Weekly et al. | |

FOREIGN PATENT DOCUMENTS

| | | | | |
|---|---|---|---|---|
| KR | 2015081463 A | * | 7/2015 | A61B 5/02 |
| WO | 2015/006364 A2 | | 1/2015 | |

OTHER PUBLICATIONS

Le, Trung et al., "Nonlinear Dynamics Forecasting of Obstructive Sleep Apnea Onsets," PLOS One, vol. 11, Nov. 11, 2016 (12 p.).
Le, Trung et al., "Wireless Wearable Multisensory Suite and Real-Time Prediction of Obstructive Sleep Apnea Episodes," IEEE Journal of Translational Engineering in Health and Medicine, vol. 1, Aug. 12, 2013 (9 p.).
Karandikar, Kunal, "Estimation of Surrogate Respiration and Detection of Sleep Apnea Events from Dynamic Data Mining of Multiple Cardiorespiratory Sensors," Jul. 2012 (91 p.).

* cited by examiner

WEARABLE THERAPEUTIC INTERVENTION DEVICE FOR SLEEP DISORDERS AND METHODS OF USE THEREOF

CROSS-REFERENCE TO RELATED APPLICATIONS

This application is a 35 U.S.C. § 371 national stage application of PCT/US2018/064408 filed Dec. 7, 2018, and entitled "Wearable Therapeutic Intervention Device for Sleep Disorders and Methods of Use Thereof," which claims benefit of U.S. provisional patent application Ser. No. 62/596,663 filed Dec. 8, 2017, and entitled "Wearable Therapeutic Intervention Device for Sleep Disorders and Methods of Use Thereof," each of which is hereby incorporated herein by reference in its entirety for all purposes.

STATEMENT REGARDING FEDERALLY SPONSORED RESEARCH OR DEVELOPMENT

Not applicable.

BACKGROUND

Obstructive sleep apnea (OSA) is a medical condition which impedes the airflow through the pharyngeal airways resulting in discontinued breathing. Typically, OSA apnea occurs due to a collapse of the tissue walls around upper airways that causes temporary shallow breathing (hypoapnea) or discontinued breathing (apnea) during sleep. OSA is the most common type of sleep apnea that affects over 18 million Americans with 2-4% of those going undiagnosed. It is estimated that about 25% of middle-aged men and 9% of middle-aged women suffer from OSA. Undiagnosed or untreated OSA can cause headaches, short term memory, stroke, insomnia, daytime fatigue, cognitive problems and could be fatal for those with cardiovascular disorders.

BRIEF SUMMARY OF THE DISCLOSURE

In an embodiment, a therapeutic device comprises a sensor positioned proximate to a user and configured to receive a plurality of signals, and a processor coupled to the sensor and configured to determine a biomarker describing a biological characteristic of the user based on the plurality of signals, and determine whether the user is likely to experience an impending sleep disorder episode within a predetermined period of time based on the biomarker. In this embodiment, the therapeutic device further comprises a power supply coupled to the sensor and the processor. Further in this embodiment, the sensor comprises a multichannel photoplethysmography (PPG) sensor. In an embodiment, the multichannel PPG sensor comprises six photodiodes and two pairs of red and infrared LEDs. Further in this embodiment, the therapeutic device further comprises one or more therapeutic components, and wherein the processor is further configured to instruct the therapeutic components to massage a body part of the user in response to determining that the user is likely to experience an impending sleep disorder episode. Further in this embodiment, the biomarker comprises at least one of a heart rate, a respiration rate, or an oxygen saturation level.

In an embodiment, a method of therapeutic intervention implemented by a therapeutic device comprises receiving, by a sensor of the therapeutic device, a plurality of signals, wherein the sensor is positioned proximate to the user, determining, by a processor of the therapeutic device, a biomarker describing a biological characteristic of the user based on the plurality of signals, and determining, by the processor, whether the user is likely to experience an impending sleep disorder episode within a predetermined period of time based on the biomarker of the user. In this embodiment, the method further comprises intermittently performing the steps of the receiving the plurality of signals, determining the biomarker of the user, and determining whether the user is likely to experience the impending sleep disorder episode while the therapeutic device is worn by the user. Further in this embodiment, the method further comprises preventing, by one or more therapeutic components of the therapeutic device, the user from experiencing the impending sleep disorder episode. Further in this embodiment, the one or more therapeutic components are actuators configured to provide a massage to a body part of the user wherein the user profile comprises a user age, weight, height, sleep event history, and a plurality of predetermined biomarker thresholds. Further in this embodiment, a power supply is coupled to the sensor and the one or more therapeutic components. Further in this embodiment, determining the biomarker for the user comprises identifying accurate peaks for the biomarker, eliminating false peaks for the biomarker, and mapping the biomarker to a value corresponding to the biomarker in trained data stored at the therapeutic device, wherein the value is used to determine whether the user is likely to experience the impending sleep disorder episode. Further in this embodiment, the sensor comprises a multichannel photoplethysmography (PPG) sensor.

In an embodiment, a sleep disorder therapy system comprises a sensor positioned proximate to a user and configured to receive a plurality of signals, and a processor coupled to the sensor and configured to determine a biomarker describing a biological characteristic of the user based on the plurality of signals, determine whether the user is likely to experience an impending sleep disorder episode within a predetermined period of time based on the biomarker, and instruct a plurality of therapeutic components to prevent the impending sleep disorder episode from occurring to the user. In this embodiment, the system further comprises a remote device located remotely from the sensor, and wherein the processor is executed at the remote device. Further in this embodiment, the sensor comprises a photoplethysmography (PPG) sensor. Further in this embodiment, the biomarker comprises at least one of a heart rate, a respiration rate, or an oxygen saturation level. Further in this embodiment, the sensor is positioned proximate to a neck of the user. Further in this embodiment, the system further comprises a power supply coupled to the sensor, and wherein the sensor comprises a photodiode. Further in this embodiment, the plurality of signals comprise a plurality of optical signals, and wherein the optical signals are used by a photodiode to determine the biomarker of the user.

Embodiments described herein comprise a combination of features and advantages intended to address various shortcomings associated with certain prior devices, systems, and methods. The foregoing has outlined rather broadly the features and technical advantages of the invention in order that the detailed description of the invention that follows may be better understood. The various characteristics described above, as well as other features, will be readily apparent to those skilled in the art upon reading the following detailed description, and by referring to the accompanying drawings. It should be appreciated by those skilled in the art that the conception and the specific embodiments disclosed may be readily utilized as a basis for modifying or designing other structures for carrying out the same purposes of the invention. It should also be realized by those skilled in the art that such equivalent constructions do not depart from the spirit and scope of the invention as set forth in the appended claims.

BRIEF DESCRIPTION OF THE DRAWINGS

For a detailed description of the preferred embodiments of the invention, reference will now be made to the accompanying drawings in which.

DETAILED DESCRIPTION OF THE PREFERRED EMBODIMENTS

Figure 1:
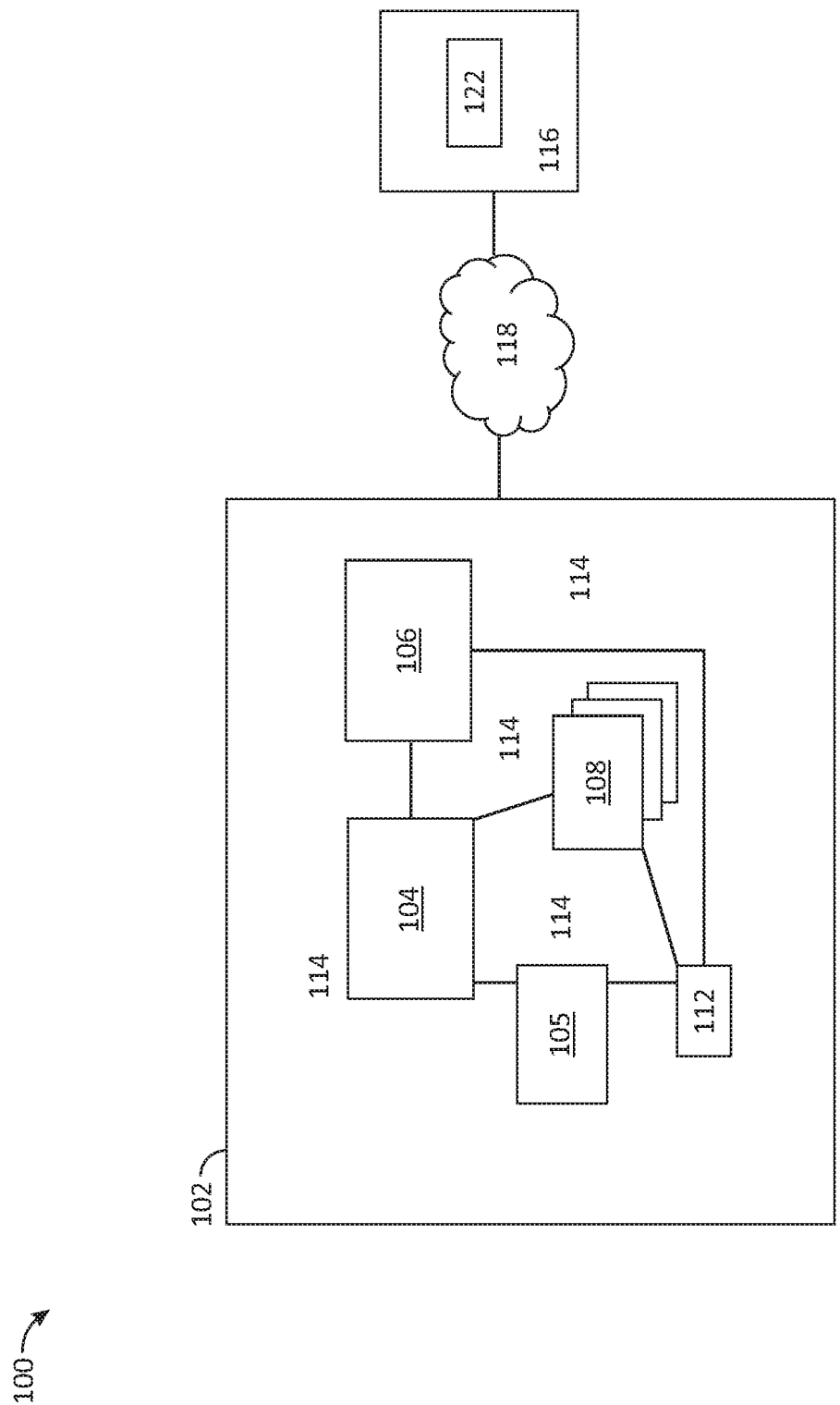
FIG. 1 is a schematic diagram of an embodiment of a sleep disorder therapy system according to various embodiments of the present disclosure.

The following discussion is directed to various exemplary embodiments. However, one skilled in the art will understand that the examples disclosed herein have broad application, and that the discussion of any embodiment is meant only to be exemplary of that embodiment, and not intended to suggest that the scope of the disclosure, including the claims, is limited to that embodiment.

Certain terms are used throughout the following description and claims to refer to particular features or components. As one skilled in the art will appreciate, different persons may refer to the same feature or component by different names. This document does not intend to distinguish between components or features that differ in name but not function. The drawing figures are not necessarily to scale. Certain features and components herein may be shown exaggerated in scale or in somewhat schematic form and some details of conventional elements may not be shown in interest of clarity and conciseness.

In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection of the two devices, or through an indirect connection that is established via other devices, components, nodes, and connections.

Obstructive sleep apnea (OSA) is a medical condition which impedes the airflow through the pharyngeal airways resulting in discontinued breathing. An individual experiencing OSA may experience an average of 60 occurrences of sleep apnea per hour or 300 occurrences of sleep apneas per night. Due to the frequent occurrences of sleep apnea per night, an individual experiencing OSA typically has a decreased sleep quality, which impacts the physiological processes necessary for the cognitive and restorative functions of the body.

For example, two of the present solutions to sleep apnea are: (i) use of CPAP (continuous positive airway pressure) and (ii) surgical methods. It is estimated that only 50% of the people prescribed with a CPAP device actually end up using the CPAP device due to various reasons, such as, for example, the machines not being covered by insurance, the machines not being portable, or the machines not being comfortable to wear while sleeping. For example, the CPAP is bulky in size and, thus, uncomfortable to wear during sleep. In addition, the CPAP causes excessive air-flow, which may lead to dryness in the nose and the throat.

Surgical methods may also be performed to reconstruct the airways that cause OSA. However, these surgical methods are associated with significant risks, and thus may not be favored by most people. Therefore, there is a need for a portable, cost-effective, state-of-the-art solution which can detect and forestall the occurrence of the apnea events.

Both of the present solutions for sleep apnea are only remedial actions, not preventative actions. Therefore, there is a vested interest in developing technologies to not only detect but to therapeutically intervene in order to mitigate (avoid) the apnea event, which may also be referred to herein as an sleep disorder episode.

The systems and methods discussed herein relate to a wearable therapeutic device and methods of use thereof to reverse an impending sleep disorder episode such as an apnea event. In an embodiment, the therapeutic device detects biomarkers measuring body vitals, such as, for example, heart rate, respiration rate, and the blood oxygen saturation (where $SpO_2$ is the Saturation of Peripheral Oxygen) extracted using a sensor. In an embodiment, the device is positioned at a body part of the user, such as, for example, the user's neck, wrist, fingertip, leg, arm, or other area where biomarkers may be measured. In an embodiment, the device determines whether a sleep disorder episode (e.g., an occurrence of OSA) is likely to occur based on the detected biomarkers. In an embodiment, the device is configured to perform therapeutic intervention on the body part of the user to prevent the sleep disorder episode from occurring. Further, the device incorporates algorithm/capability to do long-term prediction (weeks before) of sleep apnea patterns using advanced survival analysis models.

Referring to FIG. 1, a schematic diagram of an embodiment of a sleep disorder therapy system 100 according to various embodiments is shown. In this embodiment, the system 100 includes a therapeutic device 102 and a remote device 116 interconnected via network 118. The therapeutic device 102 may be a user device, such as a wearable device, which includes a storage device 104, a processor 105, a sensor 106, one or more therapeutic components 108, a power supply 112, and interior materials 114. The remote device 116 is a computing device that executes an application 122 that communicates with the therapeutic device 102 via the network 118.

The sensor 106 receives biometric data and transmits this data in the form of signals that are analyzed to determine the biomarkers. Biomarkers are biological characteristics or body vitals of the user wearing therapeutic device 102. The biomarkers may include the heart rate of the user, respiration rate of the user, and the blood oxygen saturation of the user. For example, the sensor 106 may be a photodiode, a single channel photoplethysmography (PPG) sensor 106, a multichannel PPG sensor 106, or any other type of sensor that is configured communicate with the processor 105 and the plurality of therapeutic components 108 to deliver various therapeutic treatments to the user.

A single channel PPG sensor 106 includes a single channel consisting of one or more of a red, green, or infrared (IR) Light Emitting Diodes (LEDs), and a photodiode. A multichannel PPG sensor 106 includes six photodiodes and two pairs of red LEDs and an IR. In an embodiment, the sensor 106 includes multiple sensors 106 with a ring-shaped photodiode arrangement providing multiple channels of light reflected from the skin.

The sensor 106 may be positioned anywhere on the user's body at which biometrics may be measured. For example, one or more sensors 106 may be positioned at a user's neck, wrist, fingertip, leg, arm, or forehead. The one or more sensors may be positioned proximate to a user's carotid artery, femoral artery, fingertip, or radial artery. One or more sensors 106 may be positioned at various arteries to collect the bioinformation used for the biomarkers In one embodiment, the sensor 106 is in contact with the user's skin to measure biometrics of the user. In this example, the sensor 106 is positioned on an outer surface of the therapeutic device 102. In some embodiments, the sensor 106 does not necessarily need direct contact with the user's skin to measure biometrics of the user. In this case, the sensor 106 may be positioned inside an encasing of the therapeutic device 102. For example, the therapeutic device 102 may include a cloth encasing, and the sensor 106 may be positioned on the inside of the cloth encasing. In this example, the sensor 106 may be positioned up against a body part of the user with the encasing positioned between the body part of the user and the sensor 106.

The storage device 104 is memory that stores data used by the therapeutic device 102 to measure biomarkers of the user and use the biomarkers to prevent the user from experiencing a sleep disorder episode. In an embodiment, the storage device 104 stores the biomarkers computed based on data received by the sensor 106. In an embodiment, the storage device 104 further stores profiles associated with one or more users of the therapeutic device 102. For example, the storage device 104 may store one or more default or quasi-default profiles that are pre-loaded onto the therapeutic device 102. In an embodiment, a default profile contains information for biomarkers for a general population, whereas in contrast, a quasi-default profile may take into account one or more of a user's gender, age, weight, and/or other medical conditions or sleep habits including sleep position. In an embodiment, user-specific profile may be loaded via a biomarker input to the device or to an application associated with the device, or via another type of user-specific input, and may include data related solely to that user.

User-specific profiles may be developed over time via use. For example, user-specific profiles may be determined based on past biometrics measured by the therapeutic device 102 for the user. User-specific profiles may also be determined based on previously detected sleep disorder episodes (e.g., occurrences of sleep apnea) and correlations between these sleep disorder episodes and biometrics of the user that were measured during and directly previously to the occurrence of the sleep disorder episodes. For example, the storage device 102 may store user-specific profiles for a particular user, in which the user-specific profile indicates a history of sleep disorder episodes that a user may have previously underwent. The history of sleep disorder episodes may also include the biometrics of the user during the time that the user was experiencing the sleep disorder episode. The history of sleep disorder episodes may also include the biometrics of the user during the time that led up to user was experiencing the sleep disorder episode (e.g., a pre-determined period of time prior to the user experiencing the sleep disorder episode).

The processor 105 is coupled to the storage device 104, the sensor 106, and the plurality of therapeutic components 108. The processor 105 is configured to implement the sleep disorder therapy mechanisms as disclosed herein and will be further described below with reference to FIG. 2. The processor 105 may include one or more multi-core processors and be coupled to a memory 240, which may function as data stores, buffers, etc. The processor 230 may be implemented as a general processor or may be part of one or more application specific integrated circuits (ASICs) and/or digital signal processors (DSPs).

The power supply 112 may be wirelessly chargeable, thus including a wireless charging coil (not shown), or may be a battery that employs wired charging via a cord (not shown). The power supply 112 is coupled to the storage device 104 and/or the processor 105. In some examples, the therapeutic device 102 may be solar powered such that the power supply 112 is a solar-powered or hybrid (solar plus electric) power supply. In this example, the user would be able to take the device 102 into various environments, including recreational camping environments as well as in environments where field work personnel may be deployed without reliable power generators. In FIG. 1, the power supply 112 is shown as a single supply, but may in some embodiments include a plurality of separate power supplies coupled to the sensor 106 and the plurality of therapeutic components 108 and/or the storage device 104.

The plurality of therapeutic components 108 deliver vibration and/or heat on a continuous basis or in pulsed form. In an embodiment, the therapeutic components 108 include an actuator or vibrator positioned inside the therapeutic device 102 or attached to the outside of the therapeutic device 102. In general, the therapeutic components 108 may be positioned anywhere on the therapeutic device 102 such that the therapeutic components 108 are capable of providing a massage to a body part of the user wearing the therapeutic device 102. In an embodiment in which the therapeutic device 102 is to be positioned around the neck of the user, as will be further described below with reference to FIG. 4, the therapeutic components 108 is positioned toward the front of the therapeutic device 102 proximate to where the windpipe of the user is located.

In an embodiment, a user-specific profile of the user wearing the therapeutic device 102 indicates a maximum force, pressure, or heat that may be applied to the use to provide therapeutic treatment before the user wakes up from his or her sleep. In an embodiment, a user-specific profile of the user wearing the therapeutic device 102 also indicates a minimum force, pressure, or heat that the user needs to sufficiently prevent the user from experiencing an impending sleep disorder episode.

A plurality of therapeutic treatment programs are stored in the storage device 104 or on the remote device 116. These treatment programs are executed by the plurality of therapeutic components 108. These treatment programs include a plurality of actions for the therapeutic components 108 to perform in different combinations on the body part to which the therapeutic device 102 is attached to prevent the user from experiencing a sleep disorder. For example, a treatment program may be triggered for the user in response to the measured biometrics substantially matching a predetermine data, which may be a predetermined set of conditions including threshold biomarkers indicative of an impending sleep disorder event.

Each program of the plurality of treatment programs may include a plurality of intensities (pulses/time×strength of pulse(s)), temperatures, and durations performed by the plurality of therapeutic components 108 for a predetermined period of time, as well as an indication of which therapeutic components 108 (one or more) are employed to deliver these pulses. In one example, a plurality of different treatment programs are stored on a remote device 116 that has an application 122 executable by the remote device. As shown by FIG. 1, this remote device 122 is not part of the device 102, and instead represents a server, mobile phone, tablet, wearable device, implanted device, laptop computer, desktop computer, or other device. The therapeutic device 102 is in communication with this remote device 116 via the network 118 which may be public WiFi, private wireless service, or other network.

The therapeutic device 102 may be Bluetooth and/or IR, Radio Frequency Identification (RFID), or otherwise communicatively enabled such that the therapeutic device 102 can receive information from and transmit information to the remote device 116. The application 122 take various actions responsive to device 102 use as discussed herein, and the operational information of the device 102 and its user(s), including user profiles used for biomarker analysis discussed below, may be stored on the remote device 116 and/or on the therapeutic device 102 itself and dynamically updated with use.

In some examples, the therapeutic device 102 may take a collar-like form or a pillow-like form. The therapeutic device 102 with a collar-like form secures under the head and around the neck region of a user, or to a wrist, leg, finger, or other area of a user via u-shaped bending. The u-shaped bending secures the therapeutic device 102 into place. The therapeutic device 102 with a pillow-like form is positioned under the head and neck of the user. For example, the pillow-like form may have a columnar form, a half-moon, a half-ellipse, or a coiled form. The therapeutic device 102 may be formed as any other type of wearable device, such as a tie, button, hook-and-loop, magnetics, or other wearing devices that may be secured around one or more body parts of the user. This may enable a user to move positions while sleeping without compromising the integrity of the device's operation. The components discussed herein of the system 100 may be scaled in size and rearranged in orientation in order to accommodate a plurality of user sizes (children through adult) as well as a plurality of measurement locations—neck, wrist, finger, leg, etc.

In an embodiment, the therapeutic device 102 includes interior fill material 114 that fills the form or shape of the therapeutic device 102. The interior fill material 114 facilitates securing the shape of the therapeutic device 102 while ensuring that the therapeutic device 102 is comfortable to the user. In an embodiment, an interior fill material 114 of the device 102 is selected such that one or more of a size, composition, and type of the interior fill materials 114 may be employed. For example, the interior fill materials 114 may include one or more combinations of gels, foam, microbeads, cotton, wool, down, other feathers, and synthetic materials.

The interior fill material(s) 114 performs a plurality of functions including providing comfort to the user while dissipating heat from the power supply 112, storage device 104, and/or other components of the therapeutic device 102. The interior fill materials 114 may be distributed evenly throughout the therapeutic device 102. In other examples, the interior fill materials 114 may be distributed such that a first material such as a heat-dissipating gel material may be distributed around the components that generate heat, and other fill materials or other types/volumes/densities of internal fill materials 114 may be employed in some or all regions of the therapeutic device 102. In some examples, components such as 104, 108, 112, and 106 may be encased in heat management wrappers. The interior fill materials 114 may be selected in some embodiments to be capable of being heated or chilled (e.g., if the therapeutic device 102 is placed in a freezer, refrigerator, or microwave for the comfort of the user) and returning to room temperature without degradation over a plurality of cycles. Similarly, any materials employed to form an external surface or surfaces of the therapeutic device 102, while not pictured in FIG. 1, may be selected for heat dissipation as well as overall patient comfort. While various positions are illustrated for the components such as 104, 108, 112, and 106, these are non-restrictive examples and these components may be positioned in any configuration in the device 102 to allow user comfort such that the arrangement that enables proper function of the device.

Figure 2:
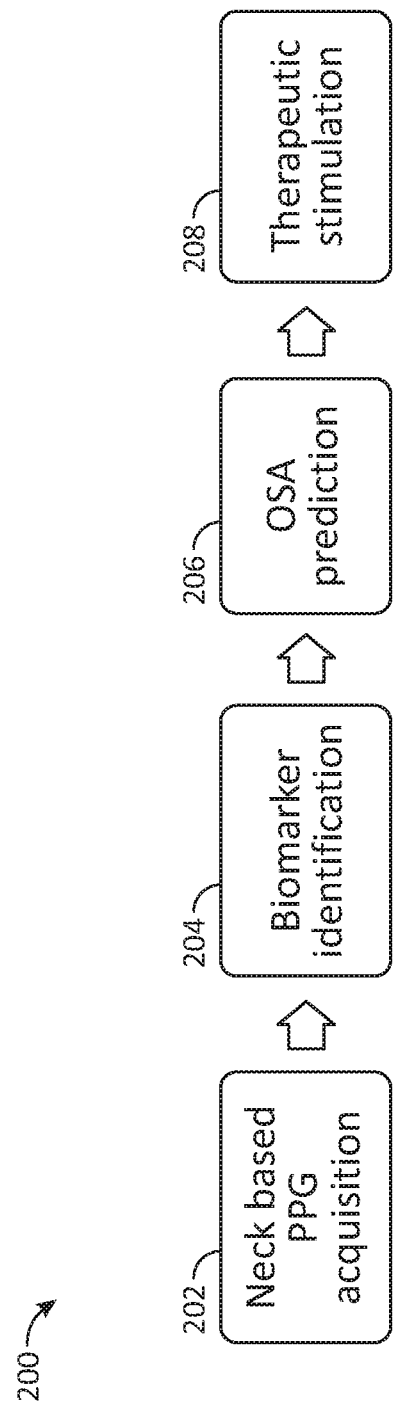
FIG. 2 is a flowchart of an embodiment of a method for preventing a sleep disorder episode using the therapy system of FIG. 1 according to various embodiments of the disclosure.

FIG. 2 is a flow chart of a method 200 for preventing a sleep disorder episode according to various embodiments of the disclosure. The method 200 may be implemented by the sleep disorder therapy system 100. At block 202, signals describing biological characteristics of a user are obtained via a sensor 106 of the therapeutic device 102 that is attached to a body part of the user. In an embodiment, the signals received by the sensor 106 are photoplethysmography (PPG) data. PPG data is optical data in the form of light that is received from a photodiode coupled to the sensor 106. The optical data is converted into digital data that may be used to determine biomarkers for the user wearing the therapeutic device 102.

In an embodiment, the PPG data is collected during each use of the sleep disorder therapy system 100 and is stored either on the therapeutic device 102 itself or on a remote device 116, such as a server computer, laptop computer, desktop computer, portable electronic device, or wearable technology. In an embodiment, the sensor 106 is configured to receive the signals (e.g., PPG data) at specific intervals at random or according to a pre-defined schedule.

At block 204, an analysis is performed on the PPG data to determine at least one biomarker of the user. As described above, a biomarker is a biological characteristic of the user, which is collected from the therapeutic device 102 worn by the user. For example, a biomarker may be the heart rate, respiratory rate, or oxygenation level ($SpO_2$) of the user.

In an embodiment, the analysis at block 204 includes implementing machine-learning algorithms such that the transducer signals received from the sensor 106 in the therapeutic device 102 are used to derive the biomarkers by extracting features from the signal. A heart rate for the user wearing the therapeutic device 102 may be determined by first determining and analyzing a plurality of peaks within discreet ranges, for example, peaks between 0.3 Hz and 10 Hz (e.g., distance $T_{HR}$ between peaks in this range). The signal obtained from the sensor 102 (e.g., the photodiode) is applied to a bandpass filter with cut-off frequencies within a predetermined range. If a normal heart rate lies between 0.5 Hz and 3 Hz, the bandpass filter may be applied with cut-off frequencies from 0.3 Hz to 3 Hz. Second, a distance ($T_{HR}$) between the determined peaks may be computed. Third, the heart rate for the user wearing the therapeutic device 102 may be computed as a function of the equation, heart rate=$60/T_{HR}$ beats/min.

During the steps of determining a heart rate for the user wearing the therapeutic device 102, a compensation method may be performed on the data that is being computed. In an embodiment, the compensation method includes determining accurate peaks and eliminating false peaks of the heart rate computed based on the data detected by the sensor 106. In an embodiment, the accurate peaks are identified by analyzing the proximity of the other peaks within the data. For example, accurate peaks may be identified based on whether other peaks are too close or too far from a current peak. In an embodiment, accurate peaks are determined and false peaks are eliminated periodically during the process of determining and analyzing the peaks of the heart rate.

The compensation method may also include compensating for errors that may have occurred in during the computation of the heart rate due to the placement of the sensors 106 of the therapeutic device 102 on a non-standard location of the user (e.g., neck, wrist, etc) (as opposed to a more standard location (e.g., finger, forehead, etc) that encounters less interference and noise). Compensating for these errors includes mapping the detected and computed data obtained from the therapeutic device 102 to trained data, which is obtained from sensors and devices positioned on prior users at the standard locations (e.g., finger, forehead, etc) that result in more accurate measurements. For example, a computed heart rate that is measured from a non-standard location and the precursors and conditions in which the heart rate was calculated was obtained may be mapped to a value in the trained data. The value indicates the heart rate would have been obtained under the same precursors and conditions, but at a standard location. The trained data obtained from the standard locations may be used instead of the computed and calculated data obtained from the non-standard location to provide for more accurate results in the computation of biomarkers.

The trained data is pre-stored in the storage device 104 of the therapeutic device 102 or pre-stored at the remote device 116 such that the trained data may be used to map the detected and computed data that may have errors to more accurate data. The trained data may be obtained based on recorded results from previous tests performed on users via sensors positioned at the standard locations that result in more accurate measurements and include less noise.

In an embodiment, the compensation mechanisms discussed above is implemented between iterations or between the steps of determining the heart rate for a user wearing the therapeutic device 102. The compensation mechanisms need not be performed after the heart rate is computed but may instead be performed during one or more iterations of computing the heart rate, to further improve the accuracy of the biomarkers computed for the user.

The respiratory rate may be determined in a manner similar to the heart rate, in which first, signal peaks within a range, such as 0.1 Hz to 0.5 Hz are identified. In some cases, a different range that overlaps with the first range may be employed to similarly calculate the user's respiration rate. Second, a distance ($T_{RR}$) between peaks may be computed. Third, a respiration rate may be computed as a function of the equations respiration rate=$60/T_{RR}$.

The respiration rate my be extracted from the computed heart rate in a manner similar to that which is described in the article submitted to the Graduate College of Oklahoma State University, entitled "Estimation of Surrogate Respiration and Detection of Sleep Apnea Events from Dynamic Data Mining of Multiple Cardiorespiratory Sensors," by Kunal Karandikar (hereinafter referred to as the "Respiration Article") which is hereby incorporated by reference in its entirety. As described in the Respiration Article, respiration signals (e.g., respiration rate) can be derived from an ECG or other types of cardiorespiratory sensors. Further, as described in the Respiration Article, measured heart sound signals can also be used to derive respiration components (e.g., respiration rate) that can be used in the computations disclosed herein.

The compensation method described above may also be implemented during the computation of the respiratory rate. Accurate peaks of the respiratory rate may be identified while eliminating false peaks of the respiratory rate. In addition, the respiratory rate, which is computed based on a sensor positioned at a non-standard location, may be mapped to a corresponding respiratory rate, which is computed based on a sensor positioned at a standard location.

The $SpO_2$ is calculated by first calculating Alternating Current (AC) and Direct Current (DC) values for signals in both the red and IR signals within a frequency range that may be similar to or the same as the range used to analyze the heart rate (0.3 Hz-10 Hz in this example). Subsequently, a ratio (R) is computed as follows: $(AC_{RED}/DC_{RED})/(AC_{IR}/DC_{IR})$, and the oxygen saturation level is calculated using standard methods based on R. For example, R may be a function of the oxygen saturation level based upon a formula $SpO_2=100-25(R)$.

The compensation method described above may also be implemented during the computation of $SpO_2$. The $SpO_2$, which is computed based on a sensor positioned at a non-standard location, may be mapped to a corresponding $SpO_2$, which is computed based on a sensor positioned at a standard location.

Once the biomarkers are determined and compensation is performed at block 204, a likelihood of a sleep disorder episode is derived at block 206. That is, based on the biomarker determinations, the likelihood that an apnea event will occur within one or more time periods as measured from the instant time of biomarker determination at block 204 is analyzed at block 206. For example, the processor 105 of the therapeutic device may be configured to analyze the biomarkers to determine whether a sleep disorder episode is likely to occur. In an embodiment in which the biomarkers are sent to the remote device 116 for processing, the application 122 executed at the remote device 116 may be configured to determine whether a sleep disorder episode is likely to occur.

In an embodiment, a determination of whether a sleep disorder episode is likely to occur is based on the detected biomarkers and predetermined data describing biomarkers that are associated with a likelihood of a sleep disorder episode occurring. The predetermined data may include biomarkers and other data indicative of an occurrence of a sleep disorder episode. For example, the predetermined data may include biological characteristics that indicate that a sleep disorder episode is likely to occur. For example, the predetermined data may include a threshold heart rate, threshold respiration rate, and a threshold $SpO_2$, such that the therapeutic device 102 is configured to determine that a sleep disorder episode is likely to occur when the detected biomarkers exceed the predetermined data thresholds. The predetermined data may also include other biological characteristics that are associated with a higher likelihood of a sleep disorder episode occurring. In an embodiment, the storage device 104 located at the therapeutic device 102 and/or the remote device 116 stores the predetermined data.

In an embodiment, the predetermined data also includes biological characteristics that indicate that a sleep disorder episode is likely to occur based on the profiles discussed above. For example, the predetermined data may also include the default profiles, which include data indicative of a sleep disorder episode for a general population without regard to gender, age, weight, or other specific criterion. The predetermined data may also include the quasi-default profiles, which data that indicates whether a sleep disorder episode is likely to occur based on a particular analysis of users of a particular gender, age group, weight range, throat weight distribution, and or other medical conditions or sleep habits. The predetermined data may also include the user-specific profiles, which includes threshold biomarkers that a particular user has exhibited in the past when experiencing a sleep disorder episode.

In an embodiment, the detected biomarkers are compared with the predetermined data to obtain a risk profile for the user wearing the therapeutic device 102. The risk profile indicates a likelihood that the user will experience a sleep disorder episode. For example, if the risk profile includes one or more elements that exceed one of the above defined thresholds, an impending sleep disorder episode may be preliminarily determined at block 206.

In an embodiment, a determination regarding a likelihood of a sleep disorder episode is made based on the methods described in the Institute of Electrical and Electronics Engineers (IEEE) document, entitled "Wireless Wearable Multisensory Suite and Real-Time Prediction of Obstructive Sleep Apnea Episodes," by Trung Q. Le, et. al., dated Jul. 18, 2013, which is hereby incorporated by reference in its entirety. In an embodiment, a determination regarding a likelihood of a sleep disorder episode is made based on the methods described in the PLOS Journal document, entitled "Nonlinear Dynamics Forecasting of Obstructive Sleep Apnea Onsets," by Trung Q. Le, et. al., dated Aug. 10, 2017, which is hereby incorporated by reference in its entirety.

If a likelihood of an apnea episode within a predetermined time period of analysis is determined to be likely to occur (for example, within 30 seconds, 1 minute, or other time intervals), then the therapeutic treatment is executed at block 208. The determination of an impending sleep disorder episode may trigger therapeutic simulation using the therapeutic components 108 at block 208.

The therapeutic components 108 may implement one of a plurality of different therapeutic treatment programs to the user wearing the therapeutic device 102. For example, the processor 105 may select a particular treatment program stored in the storage device 104 based on the biomarkers detected. The therapeutic components 108 implement the selected treatment program.

It is to be appreciated that the collection of data at block 202 is dynamic during the user's wearing of the device and may be activated by powering on the device and/or by the sensor being secured to a predetermined area of the user (artery, finger, etc.). Thus, the device is configured to measure and store data beyond the point at which therapeutic treatment is executed, and record the execution of treatment including its occurrence and specifics, to determine if apnea events occurred and when they occurred. That is, the device learns to determine if the treatment executed at block 208 was effective and may adjust future determinations of the likelihood of apnea events as well as the subsequent treatment programs executed.

Figure 3:
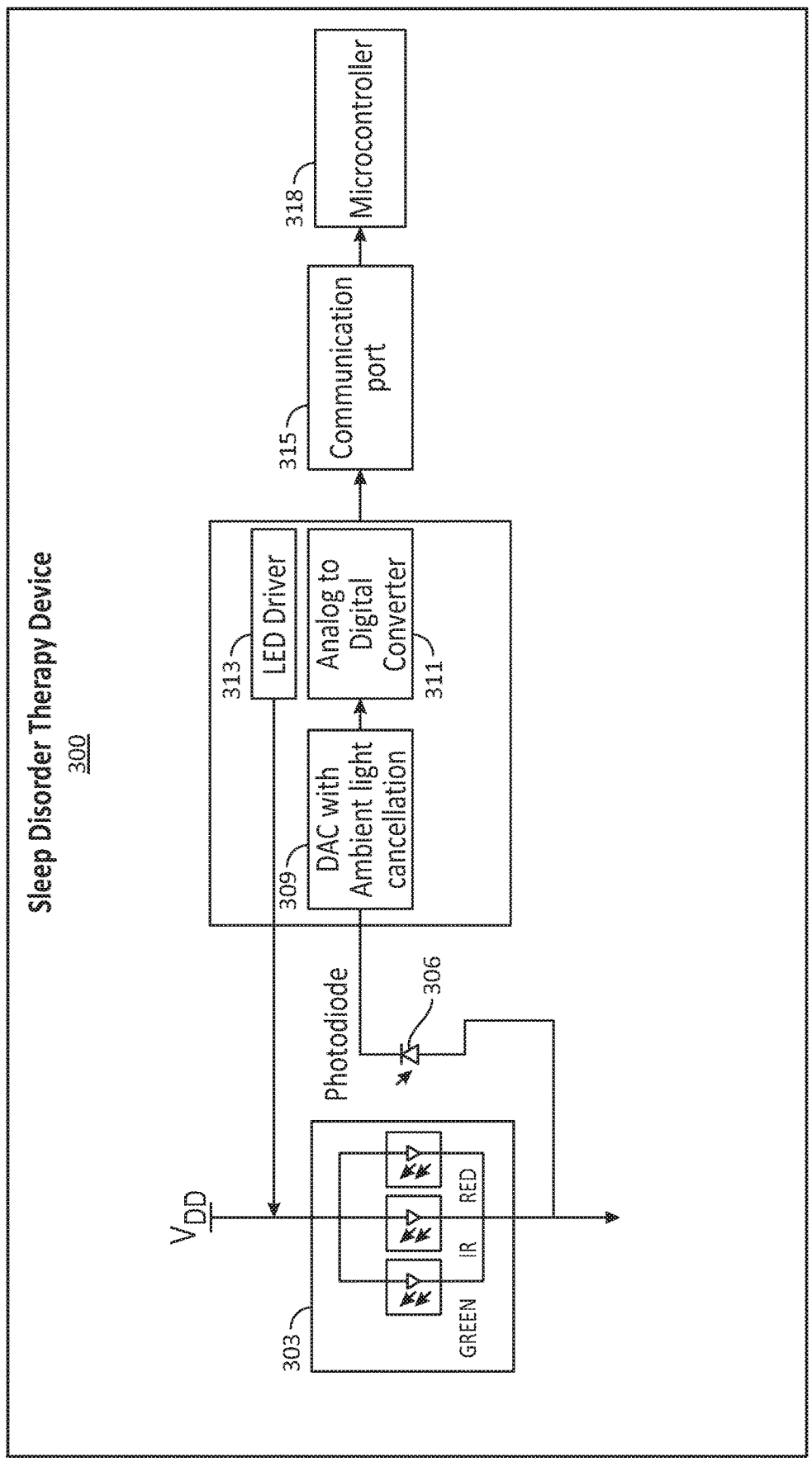
FIG. 3 is a block diagram of an embodiment of a therapeutic device according to various embodiments of the present disclosure.

FIG. 3 is a block diagram of an embodiment of a therapeutic device 300 according to various embodiments of the present disclosure. The therapeutic device 300 is similar to the therapeutic device 102, except, as illustrated in FIG. 3, the therapeutic device 300 includes LEDs 303, a photodiode 306, a digital-to-analog converter (DAC) 309, an analog-to-digital converter (ADC) 311, an LED driver 313, a communication port 315, and a microcontroller 318. As should be appreciated, the therapeutic device 300 may include additional components not otherwise shown in FIG. 3.

The LEDs 303 may include red, green, and/or infrared LEDs that are configured to emit light that is processed by the photodiode 306. The photodiode 303 operates as the sensor 106 and is configured to convert light into a current. In various embodiments, the photodiode 303 includes lenses or optical filters, and, as light is reflected off of the skin, the photodiode 303 captures the reflected light.

As discussed above, noise is typically heavily present in signals that are received from a photodiode 303 that is positioned at a non-standard location of the body, such as the neck. Using the DAC 309 and the ADC 311, the reflected light is captured and digitized, and then filtered to remove noise. The digitized signal is then transmitted via a communication port 315 to a microprocessor 318, which may be similar to the processor 105 discussed above with regard to FIG. 1.

A photodiode 306 typically collects data by sweeping light over a small range of frequencies, and then measures the spectrum of light waves that are reflected or transmitted. In an embodiment, the therapeutic device 102 tunes parameters of the photodiode 306 to obtain better quality signals, which can subsequently be used to more accurately measure biometrics of the user. In an embodiment, the photodiode 306 is optimized using several different parameters, which may be fine-tuned or periodically altered to obtain better quality signals. The parameters that are used to operate the photodiode 306 include the frequencies that are swept, a number of times that the photodiode 306 is configured to sweep over a period of time, a width of the frequency band within which the photodiode 306 is configured to sweep, a power of the LED 303 and/or other laser used to generate the light that is processed by the photodiode 306, and/or any other operating feature of the photodiode 306. These and other parameters may be adjusted as necessary before activating the therapeutic device 102 for diagnosing an impending sleep disorder episode and/or preventing the impending sleep disorder episode from occurring.

Figure 4:
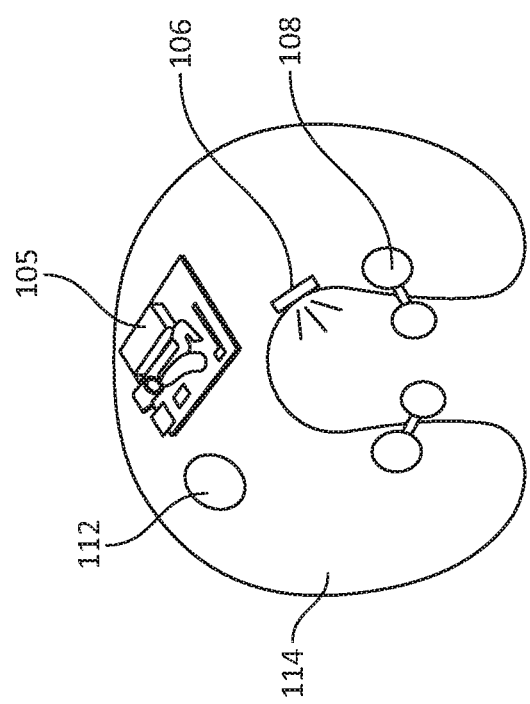
FIG. 4 is a diagram illustrating another embodiment of a therapeutic device according to various embodiments of the present disclosure.

FIG. 4 is a diagram illustrating a therapeutic device 400 according to various embodiments of the disclosure. The therapeutic device 400 is similar to the therapeutic devices 102 and 300. In particular, the therapeutic device 400 shown in FIG. 4 has a collar-like form which is configured to be secured under the head and around the neck of a user. While the therapeutic device 400 shown in FIG. 4 is shaped in a collar-like form, it should be appreciated that the therapeutic device 400 may otherwise be shaped or formed in any manner that is configured to be positioned and secured around a body part of a user.

In an embodiment, the therapeutic device 400 includes multiple component parts that are distributed internally throughout the entirety of the therapeutic device 400. As shown by FIG. 4, the therapeutic device 400 includes the processor 105, the sensor 106, power supply 112, and one or more therapeutic components 108, each of which are separately located throughout the therapeutic device 400. As should be appreciated, the therapeutic device 400 may include other components that are not shown by FIG. 4.

The separation of the each of the components of the therapeutic device 400 is advantageous for various reasons. First, heat that is generated by the performance of each of the components (the processor 105, the sensor 106, power supply 112, and one or more therapeutic components 108) of the therapeutic device 400 is distributed throughout the entirety of the device 400 to prevent the therapeutic device 400 from overheating, causing internal damage, or potentially burning the user. As shown by FIG. 4, distributing the components throughout various portions of the therapeutic device 400 may enable the user to sleep comfortably while wearing the therapeutic device 400 without the risk of overheating in a particular area of the therapeutic device 400. The fill materials 114 of the therapeutic device 400 may also prevent the therapeutic device 400 from overheating and causing damage to the device 400 itself or a risk to the user. The positioning and distribution of each of the components of the therapeutic device 400 also enables the user to more comfortably wear the therapeutic device 400 without waking up the user.

Figure 5:
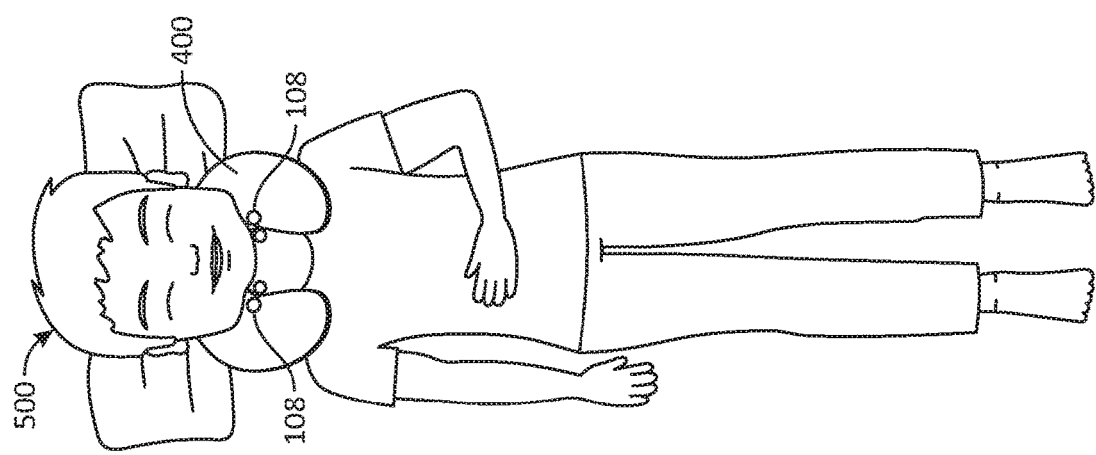
FIG. 5 is a diagram illustrating a user wearing the therapeutic device of FIG. 4 according to various embodiments of the present disclosure.

FIG. 5 is a diagram illustrating a user 500 wearing the therapeutic device 400 according to various embodiments of the disclosure. As discussed above, the therapeutic device 400 is formed in a u-shape that is ergonomically designed to comfortably fit around the neck of the user 500 without undue strain. The u-shape of the therapeutic device 400 includes a base portion that sits behind the neck of the user 500 and two raised portions that come around the neck of the user 500. The two raised portions of the therapeutic device 500 include the therapeutic components 108, which may be actuators or a vibrating device. The therapeutic components 108 are configured to provide a pulse, massage, or heat to a throat region, such as the windpipe, of the user 500 in response to the therapeutic device 400 determining that an impending sleep disorder episode is likely to occur based on biomarkers determined for the user 500.

The systems and methods discussed herein are associated with a light-weight wearable design integrated with both a PPG sensor 106 to monitor the biomarkers and a stimulation mechanism for maintaining continuous airflow through the pharyngeal airways. There are four phases of sleep, NREM1 (eyes closed, lightly asleep), NREM2 (harder to wake up, metabolic functions begin to slow), NREM3 (deep sleep, sleep through most disturbances), and REM SLEEP (dream stage, heart and respiration rate may be elevated). The therapeutic interventions and therapies discussed herein are designed to move the user no more than one sleep phase.

Figure 6:
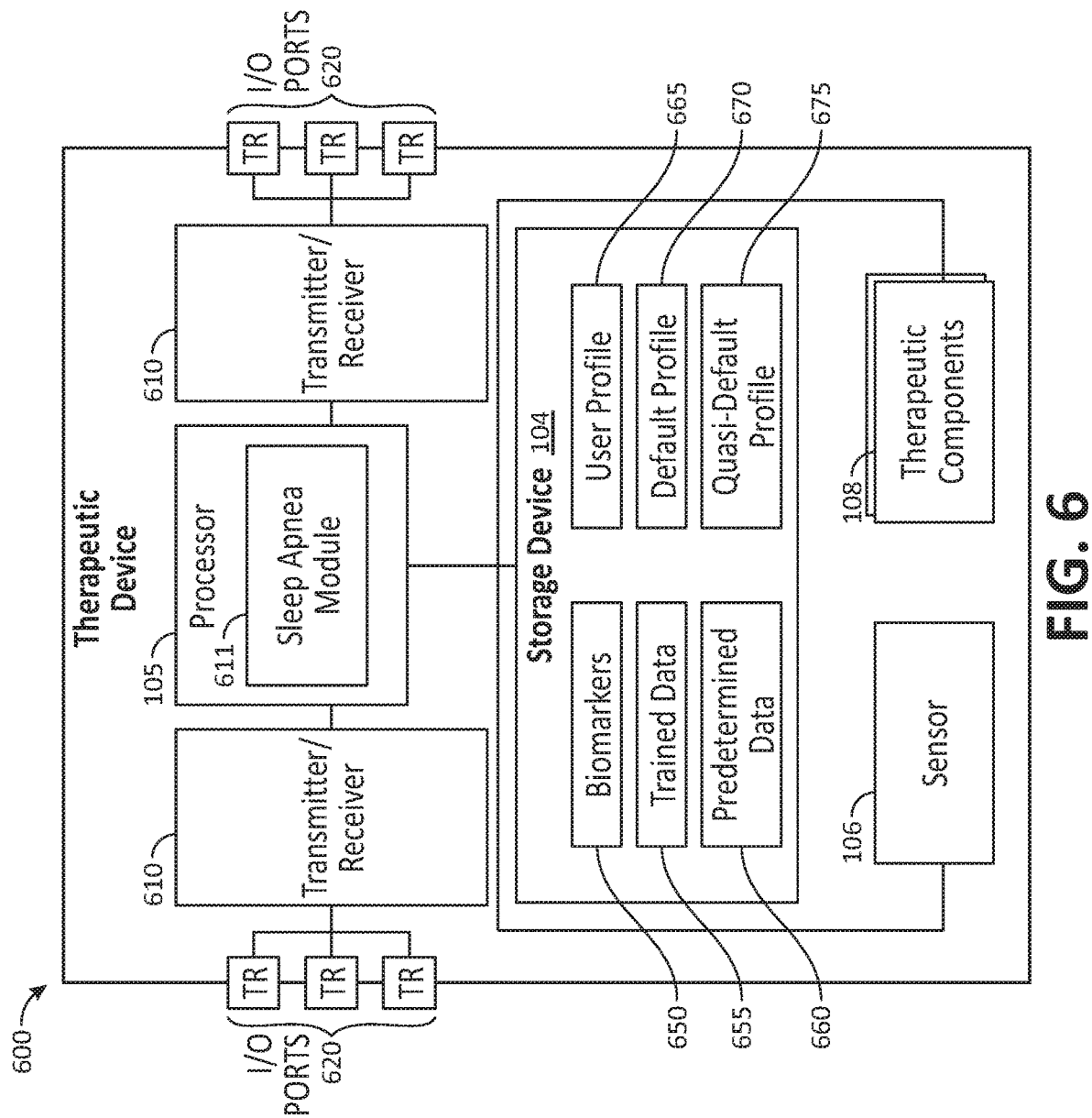
FIG. 6 is a diagram illustrating an embodiment of a therapeutic device according to various embodiments of the disclosure.

FIG. 6 is a diagram of an embodiment of a therapeutic device 600, which may be similar to the therapeutic devices 102, 300, and 400. The therapeutic device 600 implements and/or supports sleep disorder episode detection and prevention mechanisms and schemes described herein. The therapeutic device 600 may be implemented in a single device or the functionality of the therapeutic device 600 may be implemented in a plurality of device. One skilled in the art will recognize that the term device encompasses a broad range of devices of which the therapeutic device 600 is merely an example.

At least some of the features/methods described in the disclosure are implemented in an apparatus or component such as the therapeutic device 600. For instance, the features/methods in the disclosure may be implemented using hardware, firmware, and/or software installed to execute on hardware. By way of illustration, the therapeutic device 600 is configured to implement, for example, methods 700 and 800. As shown in FIG. 6, the therapeutic device 600 includes transceivers (Tx/Rx) 610, which may be transmitters, receivers, or combinations thereof. The Tx/Rx 610 is coupled to a plurality of ports 620 for transmitting and/or receiving data from the sensor 104 and/or the therapeutic components 108.

The processor 105 is coupled to each Tx/Rx 610 to process the data and determine whether a sleep disorder episode is likely to occur. The processor 105 may include one or more multi-core processors that may be implemented as a general processor or by one or more application specific integrated circuits (ASICs) and/or digital signal processors (DSPs).

In one embodiment, the processor 105 include internal logic circuits to implement the sleep apnea module 611, and may include internal logic circuits to implement the functional steps in methods 700 and 800, as discussed more fully below, and/or any other flowcharts, schemes, and methods discussed herein. As such, the inclusion of the sleep apnea module 611 and associated methods and systems provide improvements to the functionality of the device 600. In an alternative embodiment, the sleep apnea module 611 is implemented as instructions stored in the storage device 104, which are executed by the processor 105 to perform the operations of the sleep apnea module 611. Furthermore, the sleep apnea module 611 can optionally be omitted from the therapeutic device 600.

The storage device 104 may include a cache for temporarily storing content, e.g., a random-access memory (RAM). Additionally, the storage device 104 may include a long-term storage for storing content relatively longer, for example, a read-only memory (ROM). For instance, the cache and the long-term storage may include dynamic RAMs (DRAMs), solid-state drives (SSDs), hard disks, or combinations thereof. The storage device 104 stores the biomarkers 650, trained data 655, predetermined data 660, user profiles 665, default profiles 670, and quasi-default profiles 675. As described above, the biomarkers 650 are computed based on PPG data received from the sensors 106. The trained data 655 may be preloaded onto the therapeutic device 600 and includes biological characteristics associated with a sleep disorder episode measured at standard locations a user, such as a finger or a forehead of a user. The predetermined data 660 may include biological characteristics, such thresholds for each of the biomarkers, which are used to determine whether the user is likely to experience a sleep disorder episode. The user profile 665 may include biomarkers and other data specific to the user based on a history of sleep disorder episodes of the user. The quasi-default profiles 675 may include biomarkers and other data indicating an impending sleep disorder episode for individuals who are categorized based on a common gender, age, weight, sleep conditions, etc. The default profiles 670 may include biomarkers and other data indicating a sleep disorder episode for the general population.

Figure 7:
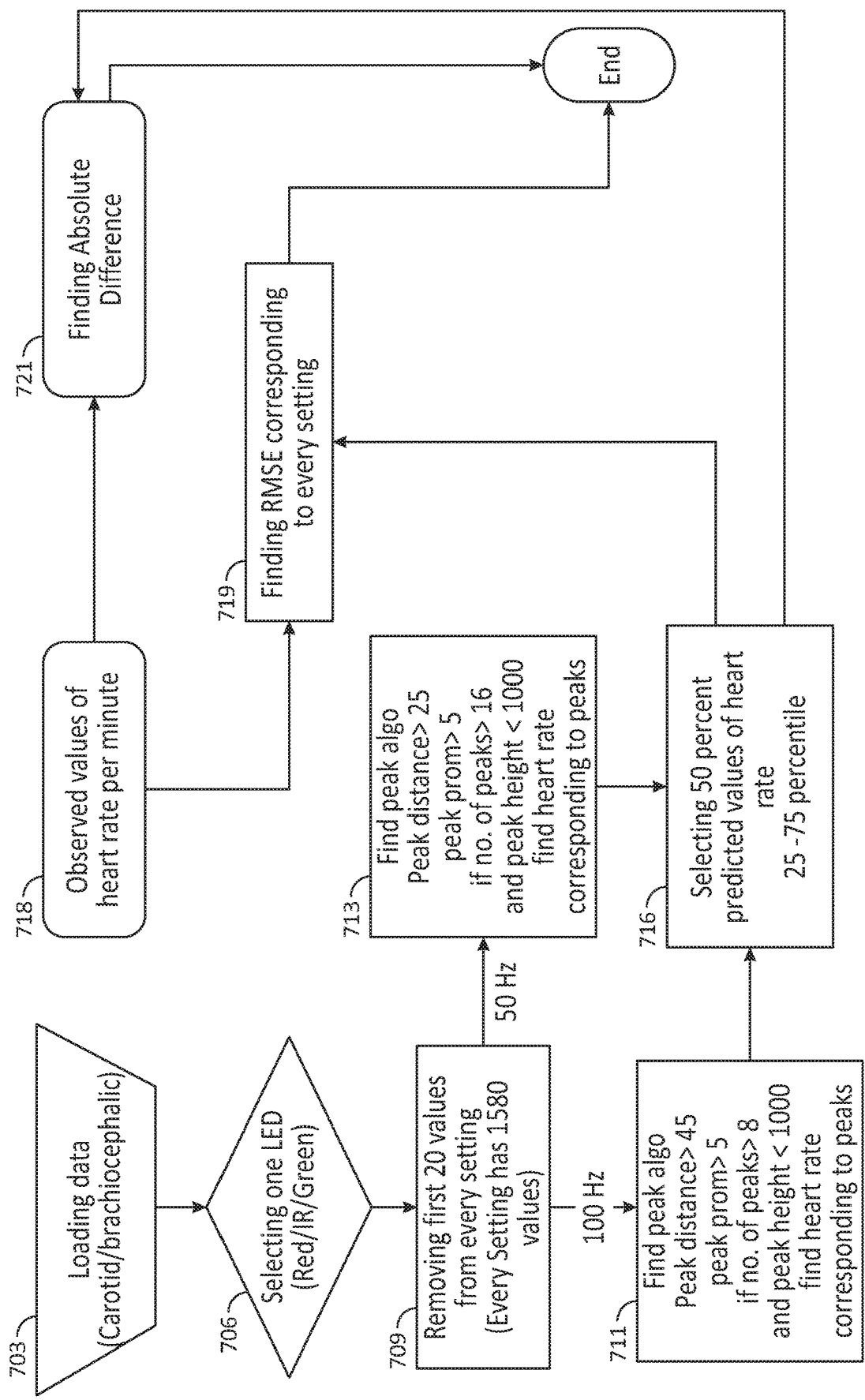
FIG. 7 is a flowchart of a method of computing a biomarker for a user wearing a therapeutic device according to various embodiments of the disclosure.

FIG. 7 is a flowchart of method 700 of computing a biomarker for a user wearing the therapeutic device according to various embodiments of the disclosure. Method 700 may be implemented by a therapeutic device, such as the therapeutic device 102, 300, 400, or 600. In an embodiment, method 700 is implemented at blocks 204 and 206 of FIG. 2.

At step 703, data collected from users wearing the therapeutic device is obtained. The data may contain electrocardiograph signals in mV. The data may be collected from sensors 106 placed on the body of the users proximate to two different arteries, such as the carotid and the brachiocephalic. Collecting data from sensors 106 positioned proximate to these arteries may be unique since most data used to sense a heart rate is collected from the wrist. Collecting data from sensors 106 positioned proximate to these arteries also help provide a better prediction of different diseases like sleep apnea. In an embodiment, data is collected every 8 minutes from each artery.

At step 706, one LED (red/IR/green) is selected. As the data is collected corresponding to the three different LEDs, each LED may be selected one at a time to perform the analysis and computations. At step 709, the first 20 values from every reading or setting may be removed. In some cases, each setting has about 1570 values). Removing the first 20 values from every setting removes noise that is related to the user's movement in the initial phases of detection.

A detrend may be performed on the data to remove any trends in the signal. A denoise may also be performed on the data to make the signal smooth. After performing the detrend and denoise, the signals may be divided depending on the frequencies (100 Hz and 50 Hz).

When the signal is 100 Hz, at step 711, a find peak function may be used with settings that the Minimum Peak Prominence=5 and the Minimum Peak Height=45. With these settings, only peaks with a prominence greater than 5 mV and with a distance between consecutive peaks being greater than 45 are marked as a peak. A peak prominence, or a prominence of a peak, refers to a minimum height of a peak. A minimum peak distance may be selected as 45 because any minimum peak distance less than 45 would mean that the heart rate for the user is more than 150 beats per minute, which is unlikely to occur when users are sitting or sleeping.

In an embodiment, signals with more than 8 peaks are carried forward. This assumption is because if the number of peaks are less than 8 in 16 seconds, then this means that the heart rate in that period of time is less than 30 beats per minute, which is not possible. In an embodiment, the signals with an mV greater than 1000 mV are replaced with the previous peak. Peaks having a maximum value of 100 mV may be ideal. However, setting the limit to 1000 mV accounts for noise patterns, while eliminating the typical noise that occurs in the range of 4000-5000 mV. The heart rate may be calculated using the distance between the peaks.

When the signal is 50 Hz, step 713 is similar to step 711, except that the minimum distance is set to 25 instead of 45. The signals with more than 16 peaks are carried forward. A number of peaks less than 16 in 32 seconds would mean that the heart rate is less than 30, which is not possible. Similar to step 711, the signals with an mV greater than 1000 are replaced with the previous peak.

At step 716, 50% of the predicted values with 25-75$^{th}$ percentile of the heart rate are selected. At steps 718-720, an absolute error of the heart rate is calculated by taking an absolute difference between a predicted mean heart rate corresponding to ever setting and a true median heart rate.

Figure 8:
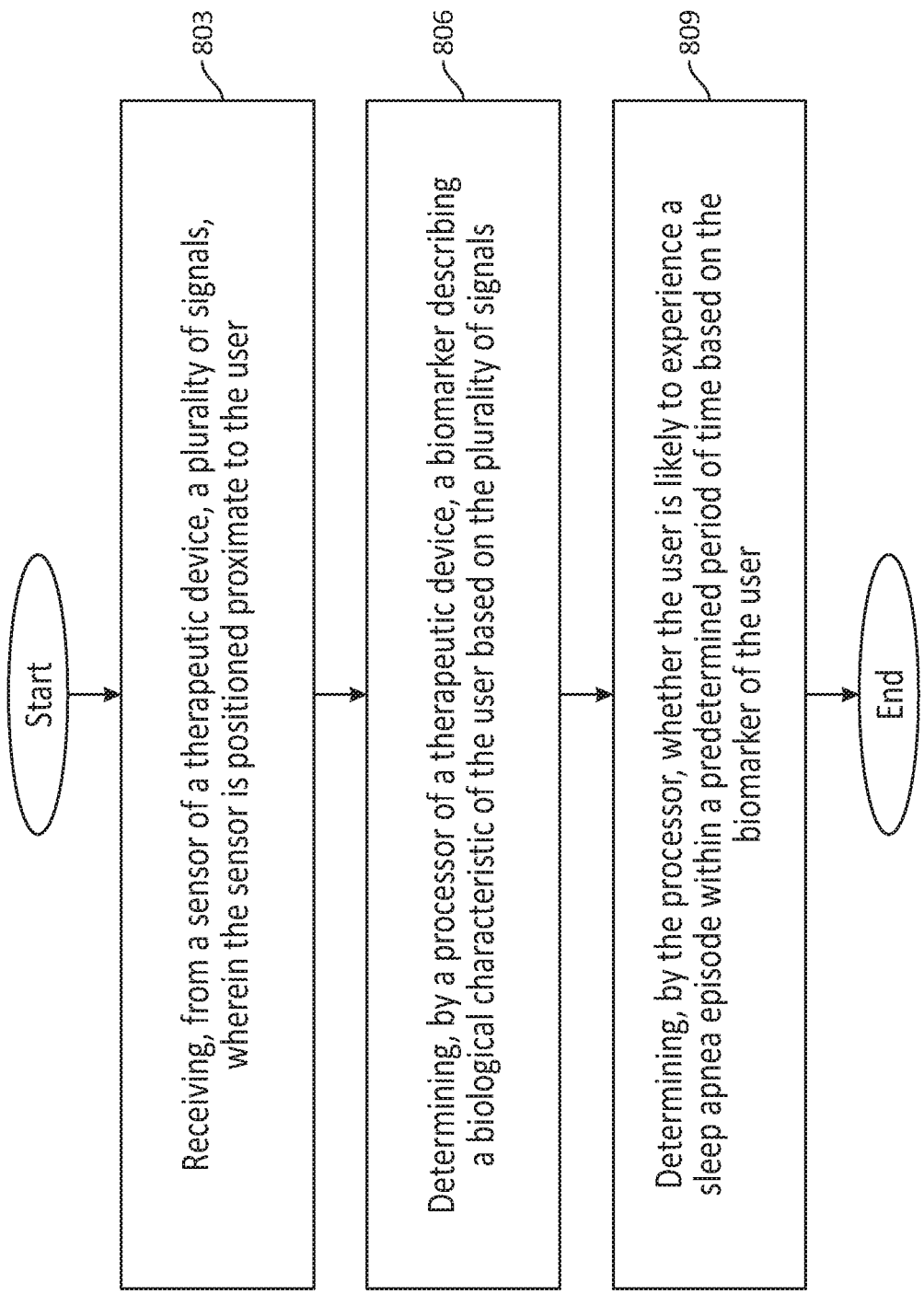
FIG. 8 is a flowchart of a method of therapeutic intervention implemented by a therapeutic device according to various embodiments of the disclosure.

FIG. 8 is a flowchart of a method 800 of therapeutic intervention implemented by a therapeutic device, such as the therapeutic device 102, 300, 400, or 600. At step 803, a plurality of signals are received from the sensor 106 of the therapeutic device. The signals may include PPG data, or optical data, that is converted into digital data.

At step 806, the plurality of signals are used to determine a biomarker 650 describing a biological characteristic of a user wearing the therapeutic device. For example, the processor 105 is configured to determine a biomarker 650 of the user based on the PPG data included in the plurality of signals.

At step 809, a determination is made as to whether the user is likely to experience a sleep disorder episode within a predetermined period of time based on the determined biomarker 650. For example, the processor 105 is configured to determine whether the user is likely to experience a sleep disorder episode within a predetermined period of time based on the determined biomarker 650. In an embodiment, the determination is made based on the predetermined data 660 and profiles 665, 670, and 675 stored at the storage device 104. The predetermined data 660 and profiles 665, 670, and 675 may also be stored at the remote device 116. In an embodiment, the method 800 further includes a step involving preventing the sleep disorder episode from occurring to the user by, for example, instructing the therapeutic components 108 to initiate a massage of a body part, such as the throat of the user.

The disruptive innovation that the therapeutic devices discussed herein offer as compared to the current available devices are at least 1) combined prognostic and therapeutic system at a low price 2) a minimized configuration with just one sensor 3) a customizable and ergonomic pillow-based sensing system.

Due to the economy of scale of the therapeutic devices discussed herein, the devices may be more easily obtained than CPAP machines or other existing devices. Further, the intervention methods executed via the therapeutic devices discussed herein can be used along with other non-invasive treatment devices such as CPAPs for effective and timely performance. Using the systems and methods discussed herein, a user's biomarkers are monitored to predict, based upon either a default profile or a user-specific profile and associated apnea event history, if an apnea event is likely to occur and that event is preempted via therapeutic intervention via the device. The outcome of this intervention, e.g., if the apnea event occurred after intervention, is also stored and employed in later analysis to determine the efficacy of the intervention and predicate analysis. The user's sleep data is dynamically detected while the therapeutic device is coupled to the user. A device may be used with many users, and may use a default profile, a quasi-default profile, or a user-specific profile. These profiles may be loaded from on-device storage and/or from off-device storage via a wireless or wired connection. The therapeutic devices discussed herein may be wirelessly enabled for communications and/or charging, and may in some examples be solar powered to allow for users to go camping or do field work across various professions.

To further illustrate various illustrative embodiments of the present invention, the following examples are provided.

Example 1

During a first phase, data was obtained from 50 volunteers to form a basis for determining a location and a method of attaching the sensors to the subjects. During a second, testing phase, overnight sleep testing was conducted for 6 healthy human subjects who were monitored during their 8-10 hour sleep for heart rate, respiration rate, and blood oxygen saturation ($SpO_2$). The overnight studies were conducted for a stretch of 8-10 hours with the subject asleep.

During the first phase, two sensors were attached on the neck of the volunteers: one on the right/left carotid arteries and another near the brachiocephalic artery (at the hollow of the neck). A Contec CMS50E was used for validation of the computed heart rate, respiration rate, and $SpO_2$ from the proposed device.

Figure 9:
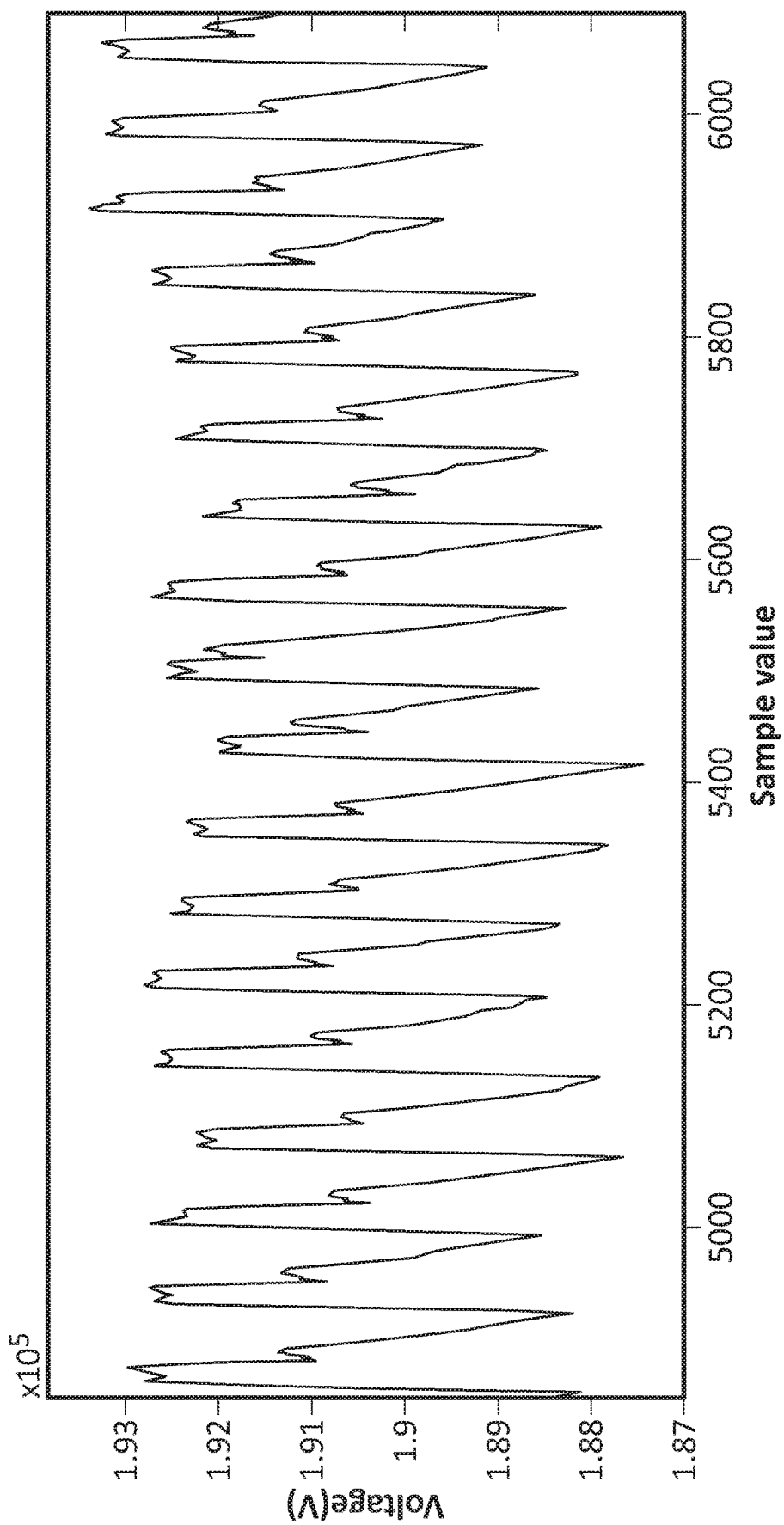
FIG. 9 is an exemplary photoplethysmography (PPG) waveform that may be acquired according to various embodiments of the disclosure.

FIG. 9 is an example PPG waveform that may be acquired using a sensor in proximity to a forehead, artery, fingertip, etc. A pulse oximeter works on the principle of PPG, which uses light to measure the blood flow through the vessels. This change can be observed in the PPG waveform as shown in FIG. 9.

Figure 10:
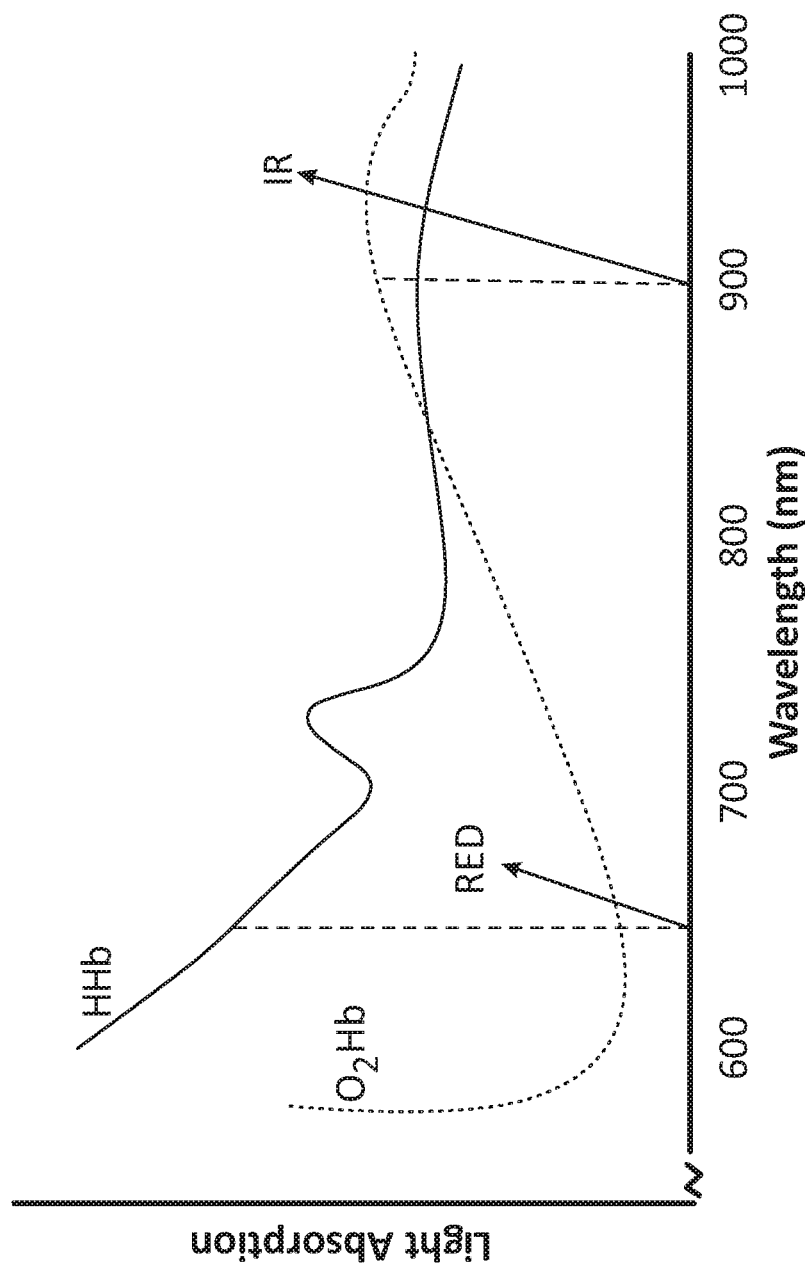
FIG. 10 is a graphical illustration of wavelength and light absorption for oxy- and deoxy-hemoglobin obtained according to various embodiments of the disclosure.

FIG. 10 illustrates a graph of wavelength and light absorption for oxy- and deoxy-hemoglobin. That is, the principle of pulse oximetry for $SpO_2$ computation is based on the difference in the absorption of LED light of various wavelengths by oxy- and deoxy-hemoglobin. At high oxygen, the absorbance of red light is lower than the absorbance of IR light. Therefore, the red signal received by the photodiode has a high DC component and a lower AC component, with the opposite being true for received IR light. Since the blood flowing in the arteries during systole and diastole vary, the amount of light received by the photodiode also changes.

Pulse oximetry has been widely used for determination of heart rate and blood oxygen saturation ($SpO_2$). A pulse oximeter works on the principle of PPG which uses light to measure the blood flow through the vessels. Since the blood flowing in the arteries during systole and diastole vary, the amount of light received by the photodiode also changes. This change can be observed in the PPG waveform as shown in FIG. 9. The Sparkfun MAX30105 sensor was attached to the neck of the subjects has a small form factor. The sensor consists of Red, IR and Green LEDs along with a Photodiode to detect the light reflected off from the blood vessels under the skin. The penetration of the LED light depends on the intensity and the wavelength of the light that is transmitted. Red and IR LEDs are used for the computation of the $SpO_2$. Since the measurement of $SpO_2$ is affected by the physical characteristics of the subjects, the pulse amplitude, sampling frequency, and the pulse widths of the LED light were varied for each of the volunteers during the first phase.

The frequency range in which the normal heart rate lies is between 0.5 Hz and 3 Hz. Therefore, the signal obtained from the photodiode is applied to a bandpass filter with cut-off frequencies of 0.3 Hz and 3 Hz. The signal peaks are obtained as shown in FIG. 9.

The principle of pulse oximetry for $SpO_2$ computation is based on the difference in the absorption of LED light of various wavelengths by oxy- and deoxy-hemoglobin. At high oxygen saturation, the absorbance of Red light is lower than the absorbance of the IR light. Therefore, the Red signal received by the photodiode has a high DC component and a lower AC component with the opposite being true for the received IR light.

The $SpO_2$ value is computed using the Beer Lambert Law which relates attenuation of light travelling through an object to the properties of absorbance of that object.

$$SpO_2 = \eta - \zeta R \quad (2)$$

where, $\eta$, $\zeta$ are constants, and R is the ratio of AC/DC (Red LED) and AC/DC (IR LED). Typical $SpO_2$ values for a healthy subject lie in the range of 93%-100%. The $SpO_2$ algorithm was applied to the signal to evaluate one value every 10 seconds. Reducing the time length required to provide one $SpO_2$ value can lead to erroneous value due to the presence of artifacts.

Figure 11:
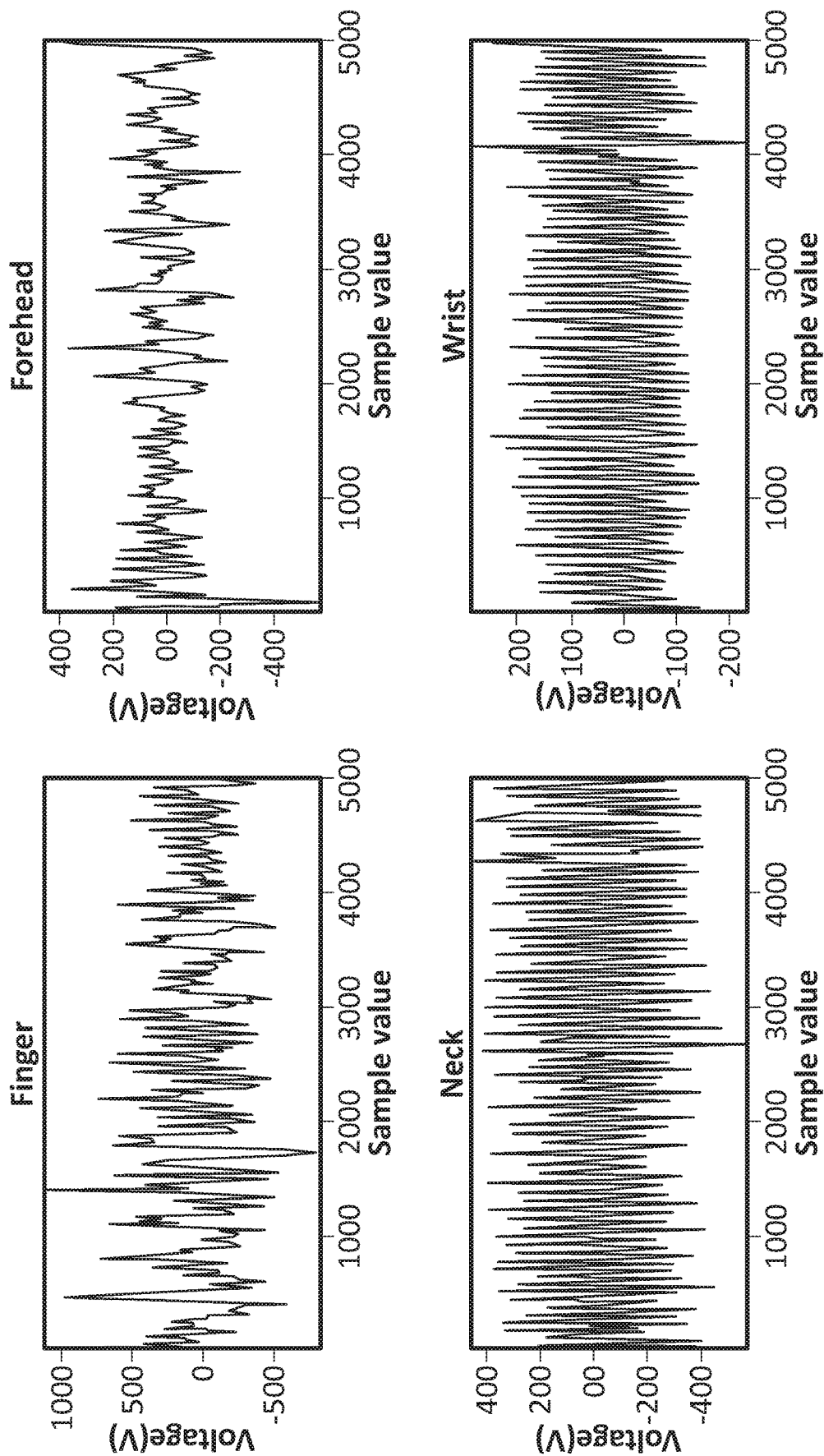
FIG. 11 is an illustration of four waveforms obtained from various positions of PPG sensors on a user obtained according to various embodiments of the disclosure.

FIG. 11 is an illustration of four waveforms obtained from various positions of PPG sensors on a user. The PPG sensor measured the pulsatile arterial blood flow in order to obtain the heart rate, respiration rate, and $SpO_2$ information. The signals were collected from various body sites before determining the optimum location. Relative pulse amplitudes from forehead, neck (right/left carotid and brachiocephalic arteries), wrist and the finger are provided in Table 1. The PPG signals obtained from the fingers and the neck have comparable amplitudes, as evident from Table 1.

TABLE 1

| Location | Relative Amplitude |
|---|---|
| Neck | 1.00 |
| Wrist | 0.54 |
| Finger | 1.05 |
| Forehead | 0.3 |

The preliminary experiments were carried out on 5 subjects of varying physical characteristics. The results of single-sensor testing are shown in Table 2. Some of factors contributing to error are: the presence of hair, fatty tissues around the neck and the skin pigmentation.

TABLE 2

| Subject | Location (Neck) | $SpO_2$ (PPG) % | Gold $SpO_2$ % | Error |
|---|---|---|---|---|
| 1 | Carotid Artery | 95.32 | 97 | 1.67 |
|   | Brachiocephalic Artery | 105.98 | 97 | −8.98 |
| 2 | Carotid Artery | 99.02 | 95 | −4.02 |
|   | Brachiocephalic Artery | 99.53 | 98 | −1.53 |
| 3 | Carotid Artery | 105.23 | 96 | −9.23 |
|   | Brachiocephalic Artery | 100.86 | 96 | −4.86 |
| 4 | Carotid Artery | 93.71 | 96 | 2.28 |
|   | Brachiocephalic Artery | 99.39 | 96 | −3.39 |

As such, the therapeutic devices discussed herein are employed to detect and mitigate apnea events with minimal discomfort of the user based upon that user's biomarkers and history of apnea events. The dynamic collection of data and resulting analysis thus enables a user with sleep apnea or other sleep disorders to mitigate the negative impact that the disorders have on their daily operation, providing a portable, cost-effective treatment.

While preferred embodiments have been shown and described, modifications thereof can be made by one skilled in the art without departing from the scope or teachings herein. The embodiments described herein are exemplary only and are not limiting. Many variations and modifications of the systems, apparatus, and processes described herein are possible and are within the scope of the invention. For example, the relative dimensions of various parts, the materials from which the various parts are made, and other parameters can be varied. Accordingly, the scope of protection is not limited to the embodiments described herein, but is only limited by the claims that follow, the scope of which shall include all equivalents of the subject matter of the claims. Unless expressly stated otherwise, the steps in a method claim may be performed in any order. The recitation of identifiers such as (a), (b), (c) or (1), (2), (3) before steps in a method claim are not intended to and do not specify a particular order to the steps, but rather are used to simplify subsequent reference to such steps.

What is claimed is:

1. A therapeutic device, comprising:
a U-shaped form configured to be positioned around a neck of a user, wherein the U-shaped form comprises:
a base portion configured to be disposed under the neck of the user while the user is lying down so as to support the user's head and neck, wherein the base portion comprises a first end and a second end;
a first raised portion extending from the first end of the base portion;
a second raised portion extending from the second end of the base portion, wherein the first and second ends are configured to at least partially circumvent the neck of the user, and wherein the base portion and the first and second raised portions together form the U-shaped form;
a sensor configured to receive a plurality of signals, wherein the sensor is in optical communication with a skin surface of the user when the U-shaped form is positioned around the neck of the user;
a first therapeutic component configured to provide a pulse or massage to the neck of the user, wherein the first therapeutic component is disposed within the first raised portion or the second raised portion;
a processor coupled to the sensor and the first therapeutic component, wherein the processor is configured to:
determine a biomarker describing a biological characteristic of the user based on the plurality of signals;
determine whether the user is likely to experience an impending sleep disorder episode within a predetermined period of time based on the biomarker and a user profile indicating a history of sleep disorder episodes of the user; and
instruct the first therapeutic component to provide the pulse or massage to the neck of the user in response to determining that the user is likely to experience the impending sleep disorder episode;
a power supply coupled to the first therapeutic component and the processor; and
a heat management material disposed around the power supply.

2. The therapeutic device of claim 1, wherein the sensor comprises a multichannel photoplethysmography (PPG) sensor.

3. The therapeutic device of claim 2, wherein the multichannel PPG sensor comprises six photodiodes and two pairs of red and infrared LEDs.

4. The therapeutic device of claim 1, further comprising a second therapeutic component, wherein the processor is further configured to instruct the second therapeutic component to provide heat to the neck of the user in response to determining that the user is likely to experience the impending sleep disorder episode.

5. The therapeutic device of claim 1, wherein the biomarker comprises at least one of a heart rate, a respiration rate, or an oxygen saturation level.

6. The therapeutic device of claim 1, wherein the first therapeutic component is disposed within the first raised portion or the second raised portion such that the first therapeutic component is configured to be proximate to the user's throat when the U-shaped form is positioned around the neck of the user.

7. The therapeutic device of claim 1, wherein the user profile further indicates an intensity limitation on the pulse or massage provided by the first therapeutic component.

8. A method of therapeutic intervention implemented by a therapeutic device, comprising:
receiving, by a sensor of the therapeutic device, a plurality of signals,
wherein the sensor, a processor, one or more therapeutic components, a power supply coupled to the processor and the one or more therapeutic components, and a heat management material disposed around the power supply are contained in a U-shaped form configured to be positioned around a neck of a user,
wherein the U-shaped form comprises a base portion and a plurality of raised portions, wherein the base portion is configured to be disposed under the neck of the user while the user is lying down so as to support the user's head and neck,
wherein the base portion comprises a first end and a second end, wherein the plurality of raised portions extend from each of the first end and the second end of the base portion such that the base portion and the plurality of raised portions together form the U-shaped form, and
wherein the sensor is in optical communication with a skin surface of the user when the U-shaped form is positioned around the neck of the user;
determining, by a processor of the therapeutic device, a biomarker describing a biological characteristic of the user based on the plurality of signals;
determining, by the processor, whether the user is likely to experience an impending sleep disorder episode within a predetermined period of time based on the biomarker of the user and a user profile indicating a history of sleep disorder episodes of the user; and
preventing, by the one or more therapeutic components disposed within one or more of the plurality of raised portions of the therapeutic device, the user from experiencing the impending sleep disorder episode.

9. The method of claim 8, further comprising intermittently performing the steps of the receiving the plurality of signals, determining the biomarker of the user, and determining whether the user is likely to experience the impending sleep disorder episode while the therapeutic device is worn by the user.

10. The method of claim 8, wherein the one or more therapeutic components are actuators configured to provide a pulse, a massage, heat, or a combination thereof to a body part of the user.

11. The method of claim 8, wherein a power supply is coupled to the sensor and the one or more therapeutic components.

12. The method of claim 8, wherein determining the biomarker for the user comprises:
identifying accurate peaks for the biomarker;
eliminating false peaks for the biomarker; and
mapping the biomarker to a value corresponding to the biomarker in trained data stored at the therapeutic device, wherein the value is used to determine whether the user is likely to experience the impending sleep disorder episode.

13. The method of claim 8, wherein the sensor comprises a multichannel photoplethysmography (PPG) sensor.

14. The method of claim 8, wherein preventing the user from experiencing the impending sleep disorder episode comprises:
- determining, by the processor, an intensity for a pulse or massage to be delivered to the user based upon an intensity limitation set forth in the user profile; and
- delivering the pulse or massage to the user at the intensity.

15. A sleep disorder therapy system, comprising:
- a U-shaped form configured to be positioned around a neck of a user, wherein the U-shaped form comprises:
  - a base portion configured to be disposed under the neck of the user while the user is lying down so as to support the user's head and neck, wherein the base portion comprises a first end and a second end;
  - a plurality of raised portions extending from each of the first end and the second end of the base portion such that the base portion and the plurality of raised portions together form the U-shaped form; and
  - a sensor configured to receive a plurality of signals, and wherein the sensor is in optical communication with a skin surface of the user when the U-shaped form is positioned around the neck of the user;
- a processor coupled to the sensor;
- a power supply coupled to a plurality of therapeutic components and the processor; and
- a heat management material disposed around the power supply,
- wherein the processor is configured to:
- determine a biomarker describing a biological characteristic of the user based on the plurality of signals;
- determine whether the user is likely to experience an impending sleep disorder episode within a predetermined period of time based on the biomarker and a user profile indicating a history of sleep disorder episodes of the user; and
- instruct the plurality of therapeutic components disposed within one or more of the plurality of raised portions to prevent the impending sleep disorder episode from occurring to the user.

16. The sleep disorder therapy system of claim 15, further comprising a remote device located remotely from the sensor, and wherein the processor is executed at the remote device.

17. The sleep disorder therapy system of claim 15, wherein the sensor comprises a photoplethysmography (PPG) sensor.

18. The sleep disorder therapy system of claim 15, wherein the biomarker comprises at least one of a heart rate, a respiration rate, or an oxygen saturation level.

19. The sleep disorder therapy system of claim 15, and wherein the sensor comprises a photodiode.

20. The sleep disorder therapy system of claim 15, wherein the plurality of signals comprise a plurality of optical signals, and wherein the optical signals are used by a photodiode to determine the biomarker of the user.

21. The sleep disorder therapy system of claim 15, wherein the plurality of therapeutic components are disposed within one or more of the plurality of raised portions such that one or more of the plurality of therapeutic components are configured to be proximate to the user's throat when the U-shaped form is positioned around the neck of the user.

* * * * *